(12) United States Patent
Kawata et al.

(10) Patent No.: US 6,858,009 B2
(45) Date of Patent: Feb. 22, 2005

(54) ULTRASONIC ANGIOSCOPE SYSTEM

(75) Inventors: Satoshi Kawata, Osaka (JP); Tadao Sugiura, Osaka (JP); Osamu Ohshiro, Nara (JP); Kunihiro Chihara, Osaka (JP)

(73) Assignee: Japan Science and Technology Corporation, Kawaguchi (JP)

( * ) Notice: Subject to any disclaimer, the term of this patent is extended or adjusted under 35 U.S.C. 154(b) by 0 days.

(21) Appl. No.: 10/333,134

(22) PCT Filed: May 16, 2001

(86) PCT No.: PCT/JP01/04064

§ 371 (c)(1),
(2), (4) Date: Sep. 29, 2003

(87) PCT Pub. No.: WO02/05716

PCT Pub. Date: Jan. 24, 2002

(65) Prior Publication Data

US 2004/0102821 A1 May 27, 2004

(30) Foreign Application Priority Data

Jul. 18, 2000 (JP) ........................................ 2000-216862

(51) Int. Cl.[7] .............................................. A61B 8/12
(52) U.S. Cl. ...................... 600/439; 600/466; 600/471; 606/7; 606/15
(58) Field of Search ......................... 600/439, 462–463, 600/466–467, 471; 606/1, 7, 15

(56) References Cited

U.S. PATENT DOCUMENTS 4,504,727 A * 3/1985 Melcher et al. ......... 219/121.62
5,651,366 A * 7/1997 Liang et al. ................. 600/439
6,022,309 A * 2/2000 Celliers et al. ................. 600/7
6,309,352 B1 * 10/2001 Oraevsky et al. ........... 600/407

FOREIGN PATENT DOCUMENTS

JP 8-168490 7/1996
JP 11-128229 5/1999

OTHER PUBLICATIONS

Acta Polytechnica Scandinavia, Applied Physics Series, No. 193, (1994), (Finland), pp. 1 to 32.

* cited by examiner

Primary Examiner—Francis J. Jaworski
(74) Attorney, Agent, or Firm—Oblon, Spivak, McClelland, Maier & Neustadt, P.C.

(57) ABSTRACT

An ultrasonic angioscope system which uses an imaging technique of sending ultrasonic waves to a portion ahead of a stricture of a blood vessel and visualizing a portion in the forward direction of the angioscope, and which uses a laser breakdown is provided. The ultrasonic angioscope system includes: a laser generating device (11) installed outside the human body; a probe (20) that introduces laser beams (13) emitted from the laser generating device (11) into a blood vessel (1) via an optical fiber (12), is set at the tip of the optical fiber (12), and has a lens (14) and a water tank (15) as a dielectric; ultrasonic-wave generating means that uses a laser breakdown (16) produced in the water tank (15); a plurality of hydrophones (18) that receive reflected waves, of ultrasonic waves emitted by the laser breakdown (16), from a stricture portion (2) of a blood vessel (1), and are disposed at the tip end of the probe (20); and means of forming a stricture-shaped image of the stricture portion (2) based on the signals received from the hydrophones (18) by a synthetic aperture method.

5 Claims, 5 Drawing Sheets

(a)

(b)

ULTRASONIC ANGIOSCOPE SYSTEM

TECHNICAL FIELD

The present invention relates to an ultrasonic angioscope system for visualizing a blood vessel in which a stricture portion is caused by using ultrasonic waves generated by the condense of lasers and the occurrence of a laser breakdown.

BACKGROUND ART

Conventionally, technologies in the above-mentioned field are disclosed as follows. That is, (1) "Handbook of medical ultrasonic devices" edited by Japan Electronic Industry published by CORONA PUBLISHING Co., Ltd. on Jan. 20, 1997, and (2) Japanese Unexamined Patent Application Publication No. 11-128229.

The conventional ultrasonic angioscope systems obtain the cross section of the blood vessel by scanning beam ultrasonic waves in the circumferential direction.

Hereinbelow, the above conventional ultrasonic angioscope systems are described in detail.

Treatments for a stricture portion of the blood vessel use a method for penetrating the lesion by penetrating a guide wiring in the blood vessel and by using a balloon inserted in the guide wiring. In this case, importantly, the wiring is sufficiently penetrated into the stricture portion. Therefore, a compact system for three-dimensionally visualizing a portion in the forward direction for actual time by ultrasonic waves.

DISCLOSURE OF INVENTION

Currently, the ultrasonic angioscopes transmit ultrasonic waves in the direction with an angle of 90° to a probe axis, and rotates the ultrasonic waves, thereby obtaining a two-dimensional image of the cross-section of the blood vessel. However, the ultrasonic angioscopes takes a long time for obtaining a three-dimensional image and does not obtain ahead information of the stricture portion because there is no method for generating the ultrasonic waves having no directivity.

Further, the conventional ultrasonic angioscopes obtain an image by generating beam ultrasonic waves by using a piezoelectric element and by scanning the beam ultrasonic waves in the circumferential direction. However, the conventional ultrasonic angioscopes have a problem to obtain only two-dimensional information of the cross section of the blood vessel.

To solve the above problems, it is an object of the present invention to provide an ultrasonic angioscope system which uses an imaging technique of sending ultrasonic waves to a portion ahead of a stricture of a blood vessel and visualizing a portion in the forward direction of the angioscope, and which uses a laser breakdown.

To accomplish the above object, according to the present invention, (1) an ultrasonic angioscope system comprises: a laser generating device installed outside the human body; a probe that introduces laser beams emitted from the laser generating device into a blood vessel via an optical fiber, set at the tip of the optical fiber, having a lens and a dielectric; ultrasonic-wave generating means that uses a laser breakdown generated in the dielectric; a plurality of hydrophones that receive reflected waves, of ultrasonic waves emitted by the laser breakdown, from a stricture portion of the blood vessel, and are disposed at the tip end of the probe; and means for forming a stricture-shaped image of the stricture portion based on the signals received from the hydrophones by a synthetic aperture method, (2) in the ultrasonic angioscope system according to (1), the dielectric includes water, deuterium water, and water containing polyethylene, (3) in the ultrasonic angioscope system according to (2), the water containing polyethylene is obtained by distributing polyethylene particles having a diameter of 50 to 1000 nm in distilled water, (4) in the ultrasonic angioscope system according to (1), the laser beam is a laser beam of Nd:YAG of 1064 nm, and (5) in the ultrasonic angioscope system according to (1), 16 to 64 hydrophones among the plurality of hydrophones are concentrically arranged on the probe.

In the ultrasonic angioscope system according to the present invention, the ultrasonic waves with a low directivity are transmitted, and waves reflected from an instrumentation target are received by a plurality of ultrasonic vibrators and are three-dimensionally visualized by a synthetic aperture method.

As transmission ultrasonic waves, the waves with the non-directivity are preferable to visualize a wide range ahead and the ultrasonic waves generated by the piezoelectric element are not used but the ultrasonic waves generated upon the breakdown of the condensed laser are used.

For the purpose of using the ultrasonic vibrator dedicated for reception, the hydrophone made of a polymer-material system having a higher reception sensitivity is utilized as a receiver.

BEST MODE FOR CARRYING OUT THE INVENTION

Hereinbelow, an embodiment of the present invention will be described in detail with reference to the drawings.

Figure 1:
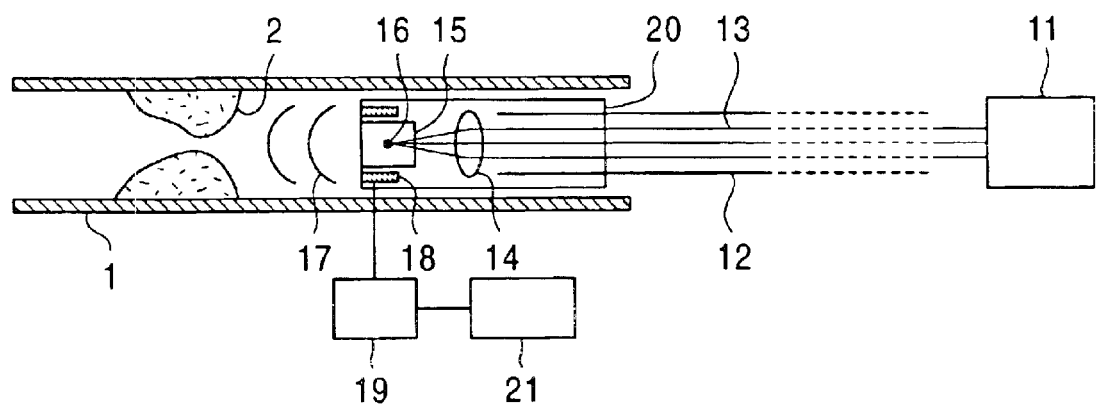
FIG. 1 is a schematic diagram showing an ultrasonic angioscope system using a laser breakdown according to an embodiment according to the present invention.

FIG. 1 is a schematic diagram showing an ultrasonic angioscope system using a laser breakdown according to an embodiment of the present invention.

Referring to FIG. 1, reference numeral 1 denotes a blood vessel. Reference numeral 2 denotes a stricture portion of the blood vessel 1. Reference numeral 11 denotes a laser generating device installed outside the human body. Reference numeral 12 denotes an optical fiber. Reference numeral 13 denotes laser beams emitted from the laser generating device 11. The laser beams 13 generated by the laser generating device 11 installed outside the human body pass through the blood vessel 1 by using the optical fiber 12 and are introduced to a desired portion. Reference numeral 14 denotes a lens for condensing the laser beams 13. Reference numeral 15 denotes a water tank as a dielectric effected by the condensed laser beams. The laser beams 13 introduced in the angioscope are condensed to the small water tank 15 in the angioscope through the lens 14 set therein. The condensed laser beams have a high energy-density and, thus, a breakdown, namely, a laser breakdown 16 is caused. The laser breakdown 1 causes light, heat, and ultrasonic waves. The ultrasonic waves (front spherical waves) from the light, heat, and ultrasonic waves are used for distance instrument. That is, the ultrasonic waves 17 with low directivity are transmitted and waves reflected from the stricture portion 2 in the blood vessel 1 are received by a plurality of high-polymer hydrophones 18 as ultrasonic vibrators. Further, the reflection waves are amplified by an amplifier 19 and, thereafter, the stricture portion 2 is three-dimensionally visualized by a three-dimensional visualizing device 21 [upon checking only the reception signal, by using a digital oscilloscope (DSO)], based on the synthetic aperture method. Reference numeral 20 denotes a probe comprising an optical fiber 12, including the lens 14 and the water tank 15.

Specifically speaking, the water tank 15 as a dielectric is filled with distilled water in which polyethylene particles (having a diameter of 200 nm) are distributed. The condensing of Nd:YAG lasers as the laser beams 13 causes the breakdown of a medium near the condensing point and, further, the laser breakdown 16 which generates the light and the ultrasonic waves occurs. Narrowing of a convergent point in this case appears the spherical ultrasonic waves with the non-directivity. The above-mentioned waveform causes little ringing. In the endoscope, the optical fiber 12 introduces to the probe 20, the laser beams from the laser generating device 11 installed outside the human body and the lens 14 condenses the laser beams to the small water tank 15 in the probe 20. The condensed lasers have a high energy-density, cause the breakdown, and generate the ultrasonic waves 17 with the non-directivity. A plurality of the hydrophones 18 for reception are installed at the edge of the probe 20 to receive echoes. The three-dimensional image in the forward direction is formed based on the echoes at points by the synthetic aperture method. This effects the diagnosis of the blood vessel and, advantageously, the image is obtained at the position where optical means such as a CCD is not used.

Figure 7:
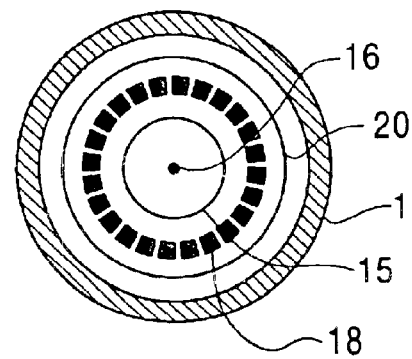
FIG. 7 is a cross-sectional view showing a laser breakdown portion according to the present invention.

As mentioned above, the lens 14 and the water tank (dielectric) 15 are installed in the probe 20 comprising the optical fiber 12. The dielectric 15 includes water, deuterium oxide, and water containing polyethylene. A laser condensing spot is within 10 $\mu$m, preferably, within 1 $\mu$m. As the spot is smaller, the ultrasonic waves have non-directivity. The laser beams 13 are laser beams of Nd:YAG having 1064 nm. Referring to FIG. 7, a plurality of hydrophones 18 for receiving the ultrasonic waves are set at the tip of the probe 20. Preferably, 16 to 64 hydrophones are arranged concentrically in the probe 20. The image is formed based on the reception signals from a plurality of hydrophones 18 by using the synthetic aperture method. Preferably, the number of the hydrophones 18 is larger.

Hereinbelow, an example will be described.

The laser beam of Nd:YAG as the laser beam 13 is 1064 nm, has a pulse width of 6 ns, and further has a repetition frequency of 10 Hz and a maximum pulse energy of 180 mJ.

Preferably, the lens 14 has a focusing distance f of 30 mm. The intensity of laser beams is adjusted by using a wavelength of $\lambda/2$ and a polarizer. The polyethylene particles having a diameter of 50 to 1000 nm are distributed in the distilled water in the water tank 15. In particular, since the water does not absorb light having the wavelength of 1064 nm, the occurrence of heat is suppressed.

The hydrophones 18 use PZT needle hydrophone.

Figure 2:
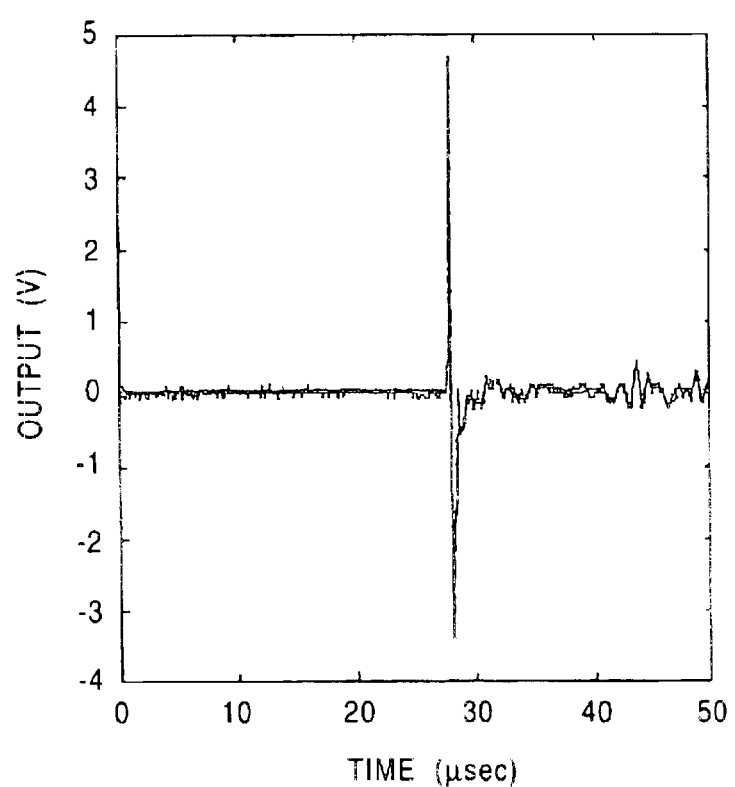
FIG. 2 is a diagram showing one example of a reception signal according to the present invention.

After generating the spherical ultrasonic waves, the generated ultrasonic waves in this case are received by using the PZT needle hydrophones and are amplified. Then, the ultrasonic waves are stored in the digital oscilloscope. FIG. 2 shows an example of the reception signal.

The input laser has a pulse of an exceedingly short width. Therefore, referring to FIG. 2, a waveform indicates an impulse response of an instrumentation system including the PZT needle hydrophones and the amplifier. As will be understood with reference to FIG. 2, the ultrasonic waves caused by the laser breakdown are single sine-waves in which one extension and one contraction are generated for a time of 0.2 $\mu$sec. Upon generating the spherical waves, the reflection waves generated in accordance therewith have no directivity. Waves after a high peak are not ringing seen in the ultrasonic waves generated by the ceramic-system vibrator but are waves reflected from the water surface or from the bottom of the water tank. Therefore, large ringing does not exist in the instrumentation system.

Figure 3:
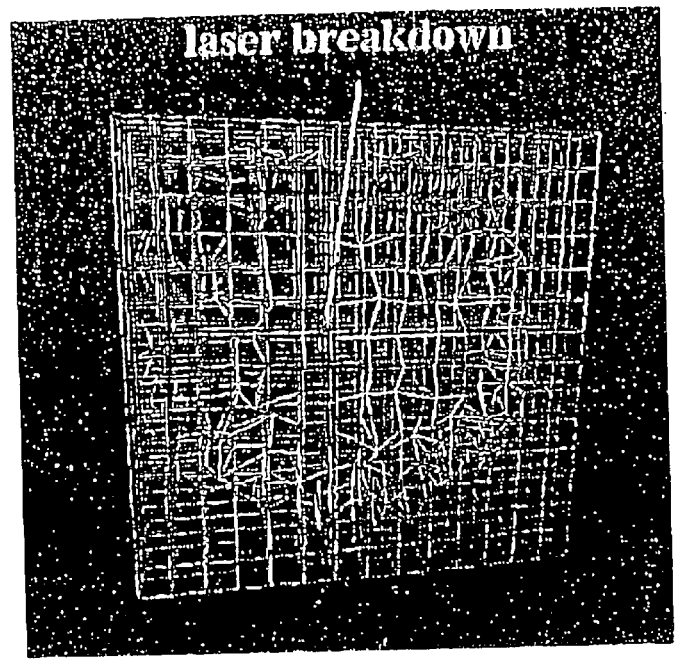
FIG. 3 is a diagram showing a status of the propagation of ultrasonic waves using the laser breakdown according to the present invention.

Further, the ultrasonic waves generated due to the breakdown are measured at a plurality of points and the wave surface propagated from the points are drawn. FIG. 3 shows an example thereof. FIG. 3 shows an acoustic field after approximately 35 $\mu$sec from the occurrence of the laser breakdown.

The laser breakdown is caused at the center point and the top of the lattice indicates an instrumentation point. A distortion of the lattice indicates the size of the reception signal at the instrumentation point. Thus, the waves are isotropically propagated. That is, the occurrence of the spherical waves is confirmed.

Figure 4:
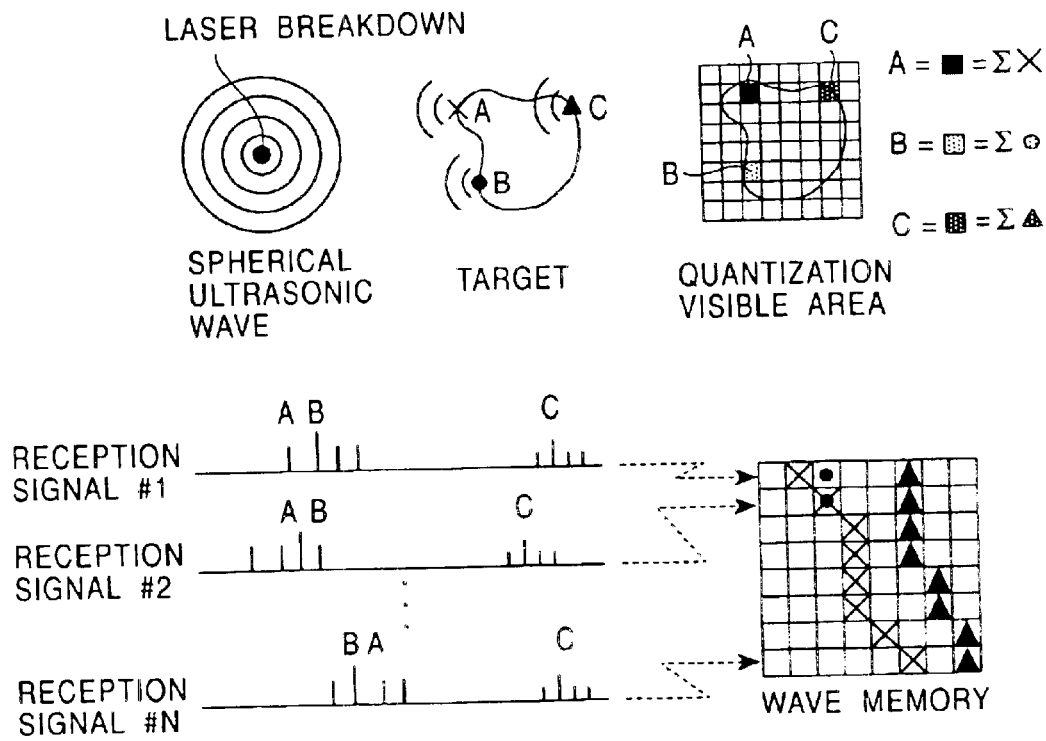
FIG. 4 is a diagram showing an image reconstructing method according to the present invention.

Referring to FIG. 2, upon reconstructing the image by using the ultrasonic waves generated due to the laser breakdown, the ringing is extremely small and data from the quantized instrumentation point is assumed as a pulse train. Since the ultrasonic waves have the non-directivity as shown in FIG. 3, it is characterized in that the consideration of weighting is not necessary upon adding the data. Thus, the image reconstruction is performed by using the reconstruction algorithm. FIG. 4 is an explanatory diagram of a method of the image reconstruction.

Figure 5:
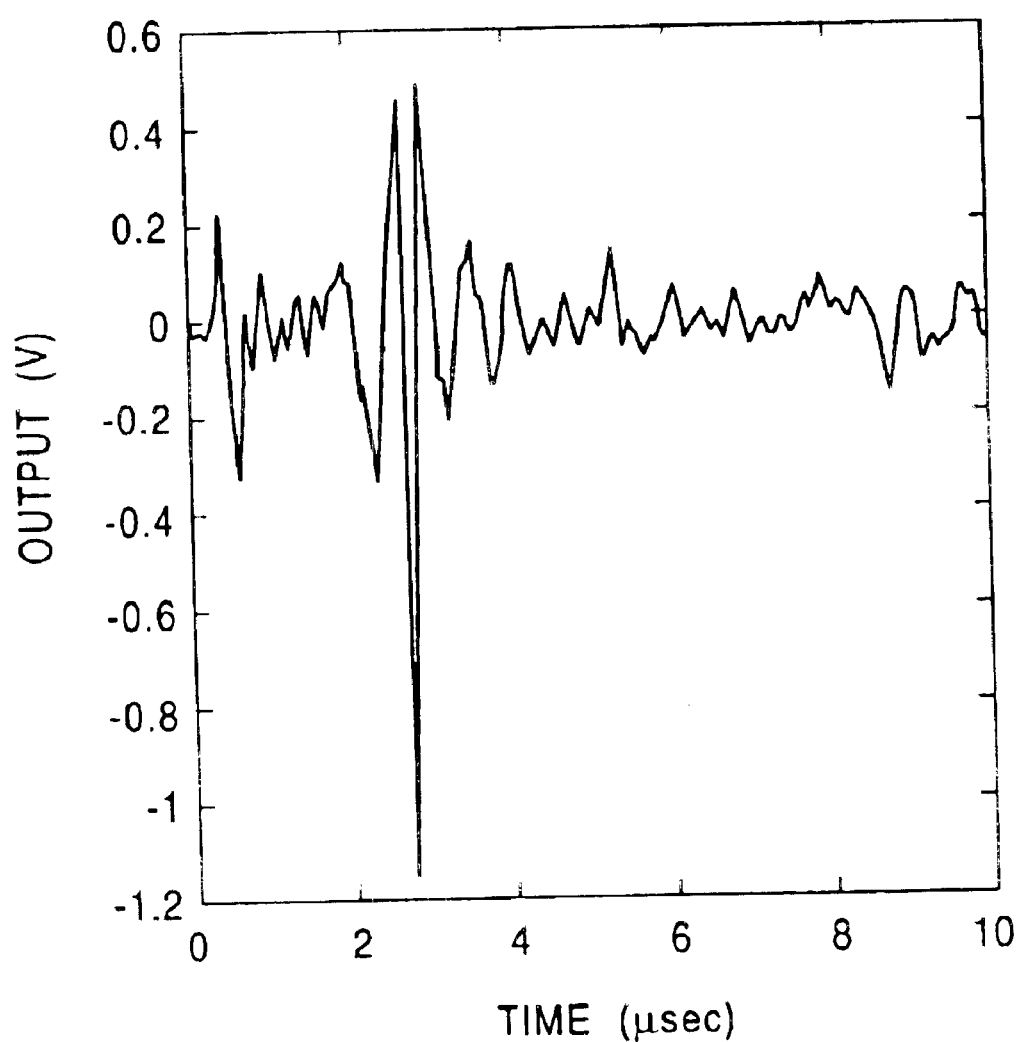
FIG. 5 is a diagram showing a waveform transmitted from an instrumentation target according to the present invention.

Herein, a hexangular wrench having a length of several centimeters (cm) is selected as an instrumentation target, is arranged in the water tank, and the reflection wages are measured at a plurality of points by using the PZT needle hydrophones. FIG. 5 shows an example of waveforms after amplification.

Figure 6:
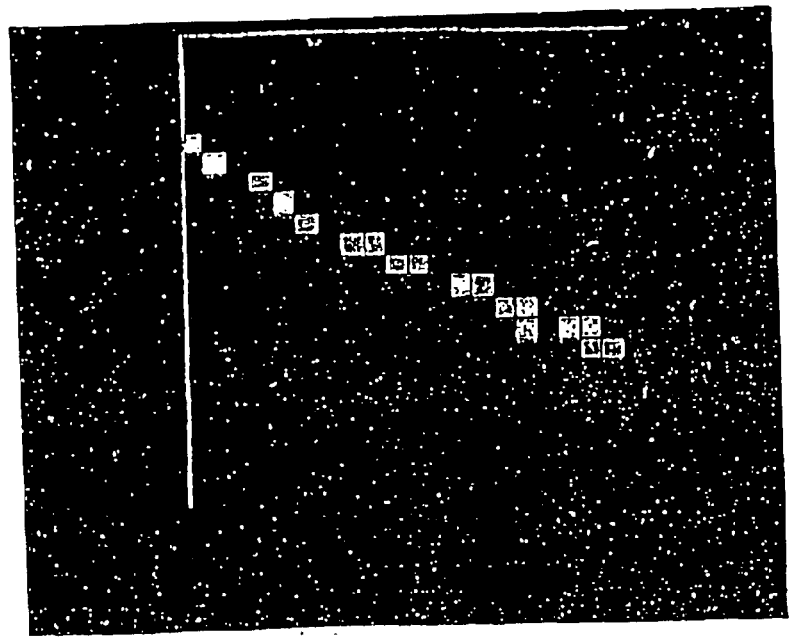
FIG. 6 is a diagram showing a result of reconstructing the image using the laser breakdown according to the present invention.
Figure 6:
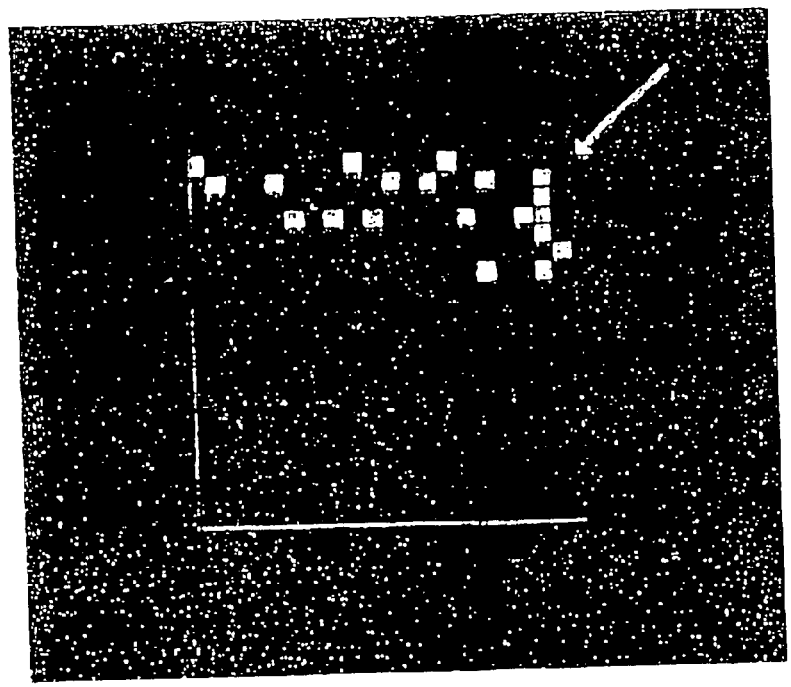

Although the reflection signal has a weak intensity as compared with the directly received signal, it has an amplitude sufficient to the three-dimensional instrumentation. Herein, the signal is subjected to the image reconstruction using the simple common-mode addition. FIG. 6 shows a result of reconstructing the instrumentation target.

FIG. 6(a) shows the three-dimensional image of the instrumentation target in the top view, in which a long and thin portion is reconstructed. FIG. 6(b) shows a bending state of a portion shown by an arrow. The use of the spherical waves obtains a high picture-quality even in the simple image reconstructing algorithm.

Figure 8:
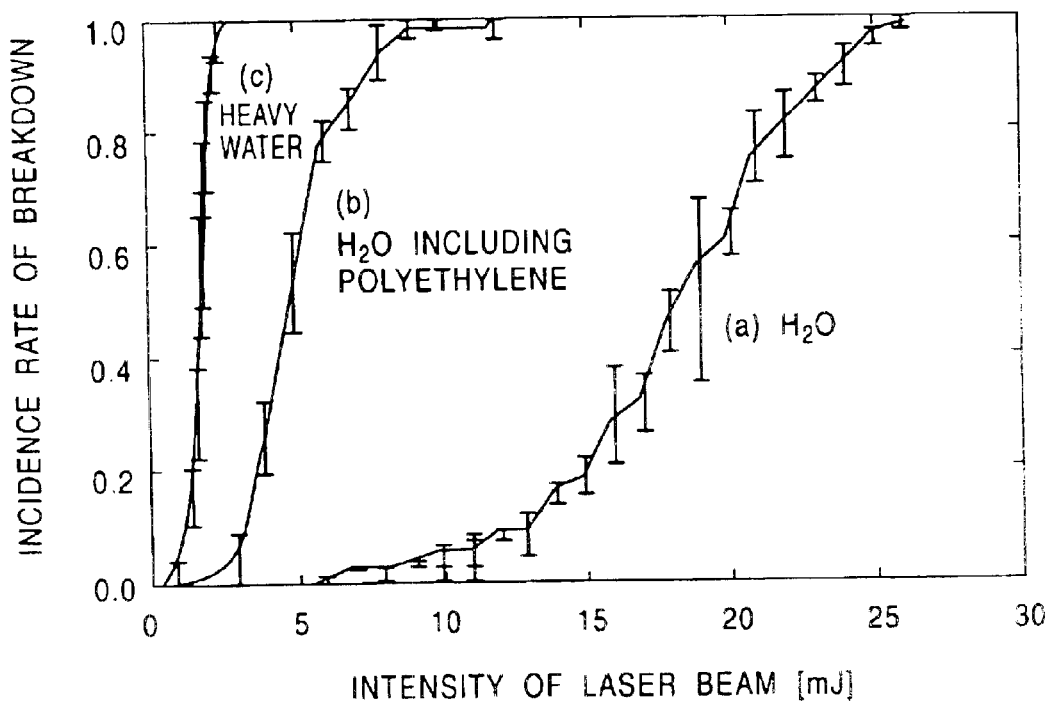
FIG. 8 is a diagram showing an incidence rate of a laser induced breakdown according to the present invention.

FIG. 8 is a diagram showing the result of measuring the incidence rate of the breakdown upon changing the laser beam intensity. Referring to FIG. 8, a result (a) of the incident rate of the distilled water ($H_2O$), a result (b) of the incident rate upon distributing polystyrene (PS) (having a particle diameter of 1 μm) in the water, and a result (c) upon using deuterium oxide ($D_2O$) are shown. As will be understood, the addition of the polystyrene (having a particle diameter of 1 μm) to the distilled water or the replacement with the deuterium oxide extremely increases the incident rate of the breakdown even by low incident-laser-power. Thus, the ultrasonic waves can safely be generated by decreasing the energy necessary for the laser induced breakdown.

The present invention is not limited to the above-described embodiment and can variously be modified based on the essentials of the present invention, and the various modifications are not excluded from the range of the present invention.

As described in detail, according to the present invention, the following advantages are obtained.

(A) An ultrasonic angioscope system is constructed for sending ultrasonic waves to a portion ahead of a stricture portion of a blood vessel and visualizing a portion in the forward direction of the angioscope without fail.

(B) The ultrasonic waves caused by the laser breakdown are sent and have no directivity, therefore, the wide range in the forward direction is visualized, and this is extremely effective for the diagnosis in the blood vessel.

(C) The ultrasonic waves caused by the laser breakdown are pulse-shaped without ringing and therefore the image having an exceedingly high resolution is reconstructed.

Industrial Applicability

The ultrasonic angioscope system according to the present invention observes the wide range of the stricture portion in the forward direction, which is not optically visualized, and is preferable to the diagnosis and the treatment using the angioscope. Further, expectatively, the ultrasonic angioscope system is used for industrial endoscopes.

What is claimed is:

1. An ultrasonic angioscope system comprising:
   (a) a laser generating device installed outside the human body;
   (b) a probe that introduces laser beams emitted from said laser generating device into a blood vessel via an optical fiber, set at the tip of the optical fiber, having a lens and a dielectric;
   (c) ultrasonic-wave generating means that uses a laser breakdown generated in the dielectric;
   (d) a plurality of hydrophones that receive reflected waves, of ultrasonic waves emitted by the laser breakdown, from a stricture portion of the blood vessel, and are disposed at the tip end of said probe; and
   (e) means for forming a stricture-shaped image of the stricture portion based on the signals received from the hydrophones by a synthetic aperture method.

2. An ultrasonic angioscope system according to claim 1, wherein said dielectric includes water, deuterium water, and water containing polyethylene.

3. An ultrasonic angioscope system according to claim 2, wherein said water containing polyethylene is obtained by distributing polyethylene particles having a diameter of 50 to 1000 nm in distilled water.

4. An ultrasonic angioscope system according to claim 1, wherein said laser beam is a laser beam of Nd:YAG of 1064 nm.

5. An ultrasonic angioscope system according to claim 1, wherein 16 to 64 hydrophones among said plurality of hydrophones are concentrically arranged on said probe.

\* \* \* \* \*